United States Patent [19]

Cobb

[11] 4,179,472

[45] Dec. 18, 1979

[54] CATALYTIC ALKYLATION OF ALKYL-SUBSTITUTED AROMATICS WITH MONOOLEFINS

[75] Inventor: Raymond L. Cobb, Bartlesville, Okla.

[73] Assignee: Phillips Petroleum Company, Bartlesville, Okla.

[21] Appl. No.: 969,600

[22] Filed: Dec. 14, 1978

[51] Int. Cl.$^2$ ............................................. C07C 3/52
[52] U.S. Cl. .................................. 585/452; 585/411; 585/453
[58] Field of Search ............ 260/668 B, 671 R, 671 C

[56] References Cited

U.S. PATENT DOCUMENTS

| | | | |
|---|---|---|---|
| 2,688,044 | 8/1954 | Pines et al. | 260/668 B |
| 2,721,886 | 10/1955 | Pines et al. | 260/668 B |
| 2,849,508 | 8/1958 | Pines | 260/668 B |
| 3,691,242 | 9/1972 | Cheng et al. | 260/668 B |
| 4,034,052 | 7/1977 | Puskas | 260/671 C |

*Primary Examiner*—Veronica O'Keefe

[57] ABSTRACT

A process whereby alkyl substituted aromatics are alkylated with a monoolefin in the presence of an alkali metal catalyst and a promoter composition selected from the group consisting of (1) biphenyl and a conjugated diene, (2) biphenyl, a conjugated diene, and a tertiary amine, and (3) naphthalene and a tertiary amine.

38 Claims, No Drawings

CATALYTIC ALKYLATION OF ALKYL-SUBSTITUTED AROMATICS WITH MONOOLEFINS

This invention relates to an improved process for the catalytic alkylation of alkyl-substituted aromatics with monoolefins. In another aspect this invention relates to an improved process for preparing tert-amyl benzene by the alkali metal catalyzed alkylation of cumene with ethylene.

The alkylation of alkyl-substituted aromatics with monoolefins has been the subject of a number of investigations and patents. Although different catalyst systems have been proposed for this process, an alkali metal catalyst system has been of particular interest since it permits alkyl aromatics with a benzylic carbon having a hydrogen substituent to be alkylated in the alkyl side chain. Much of the effort in this field has been directed toward discovering promoters that would increase the conversion and selectivity of the alkali metal catalyzed reaction.

An object of the present invention is to improve the conversion rate of the alkali metal catalyzed reaction.

Another object of the present invention is to improve the conversion rate of the alkali metal catalyzed reaction without adversely affecting the selectivity to desirable products.

Still another object of the present invention is to provide a process which enables the alkylation to proceed at a lower reaction temperature.

Other aspects, objects, and advantages of the present invention will become more apparent upon review of the following disclosure.

In accordance with the instant invention a process is provided comprising reacting a monoolefin hydrocarbon with an alkyl aromatic compound in the presence of an alkali metal catalyst and a promoter composition selected from the group consisting of (1) biphenyl and a conjugated diene, (2) biphenyl, a conjugated diene, and a tertiary amine, and (3) naphthalene and a tertiary amine.

Broadly, the type of alkyl aromatic compounds for which the present invention is applicable include any suitable alkyl aromatic compounds having a hydrogen atom bonded to at least one benzylic carbon of at least one alkyl group. Examples of suitable alkyl aromatic compounds include toluene, xylene, ethylbenzene, isopropylbenzene, n-propylbenzene, n-butylbenzene, isobutylbenzene, sec-butylbenzene, mesitylene, tetralin, and the like, and mixtures thereof. While the alkyl aromatic compounds can have other substituents which are unreactive under the alkylation conditions, it is preferred that the alkyl aromatic compounds be hydrocarbons. The especially preferred alkyl aromatic hydrocarbons are those having 1 to 4 alkyl substituents where each such alkyl substituent has 1 to 20 carbon atoms.

The monoolefin hydrocarbons include all those generally recognized as being suitable for alkali metal catalyzed alkylations of alkyl aromatics. Examples of typical such monoolefins include ethylene, propylene, 1-butene, isobutylene, 1-pentene, 1-hexene, 2-hexene, 3-hexene, 1-heptene, 2-heptene, 3-heptene, the four normal octenes, the four normal nonenes, 3-methyl-1-butene, 2-methyl-2-butene, tetramethylethylene, 1-methylcyclohexene, 1-ethylcyclohexene, 1-(1-propyl)-cyclohexene, 1,2-dimethylcyclohexene, 1,4-dimethylcyclohexene, 1,3,5-trimethylcyclohexene, and the like, and mixtures thereof. Generally for most syntheses ethylene and propylene are the preferred alkylating agents.

The alkali metals, viz. lithium, sodium, potassium, rubidium, and cesium are not equally active as catalysts. Generally, the activity of the alkali metals increases with their atomic weight. The more plentiful sodium and potassium, and mixtures thereof, such as sodium-potassium alloys, are currently preferred. Since sodium generally requires higher reaction temperatures the presently especially preferred alkali metal is potassium or a sodium-potassium alloy.

The alkali metal can be employed in any suitable form. Preferably in order to maximize surface area the alkali metal is employed in a particulate, powdered, or finely divided form. In an especially preferred embodiment the alkali metal is in a colloidal or near colloidal form, e.g. having average particle size in the range of about 0.5 to 1000 millimicrons. The preferred sodium-potassium alloys are those which are typically liquid at room temperature, i.e those having 40 to 90 weight percent potassium. The alloy containing 78 weight percent potassium is especially preferred because it is an eutectic.

The conjugated diene hydrocarbons useful in promoters of this invention include those containing 4 to 12 carbon atoms per molecule. Those containing 4 to 8 carbon atoms per molecule are preferred. Examples of such dienes include 1,3-butadiene, 2,3-dimethyl-1,3-butadiene, piperylene, 3-butyl-1,3-octadiene, 2-phenyl-1,3-butadiene, and the like and mixtures thereof.

The term tertiary amine as used in this disclosure and in the appended claims denotes those amines having three hydrocarbyl radicals attached to each nitrogen. Generally it is preferred to employ tertiary amines having no more than 60 carbon atoms per molecule. The presently preferred amines are those materials having the formula

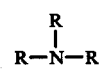

or the formula

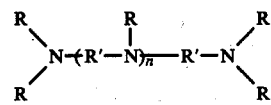

where R is a hydrocarbon radical of 1 to 6 carbon atoms, R' is a divalent hydrocarbyl radical of 1 to 6 carbon atoms, n is an integer in the range 0 to 6, and each R and R' can be the same or different. Typical tertiary amines corresponding to formula I are: trimethylamine, tri-ethylamine, tri-n-propylamine, tri-n-butylamine, tri-amylamine, dimethylbutylamine and trihexylamine. Typical polyalkylated polyamines corresponding to formula II are: N,N,N',N'tetramethylmethylenediamine, N,N,N',N'-tetraethylethylenediamine, N,N,N',N'-tetramethylethylenediamine, N,N,N',N'-tetrapropylpropylenediamine, N,N,N',N',N''pentamethyldimethylenetriamine, N,N,N',N',N''-pentamethyldiethylenetriamine, and the like and mixtures thereof. Other tertiary amines within the scope of this invention but not represented by the general formulas listed above are such tertiary amines as triethylenediamine.

The reaction conditions employed in the instant invention can vary widely depending upon the particular monoolefin and alkyl aromatics employed, the products desired, and the yields desired. Generally, the reaction temperature will be in the range of about 125° C. to about 225° C., preferably about 140° C. to about 175° C. Generally the pressure is maintained at a level sufficient to maintain the reactants in the liquid phase. Typically the reaction would thus be conducted with the pressure in the range of about 50 to about 1000 psig, preferably about 250 to about 600 psig, though higher pressures, e.g. as high as even 1200 psig, may be employed if desired, depending upon the reactants chosen, how the reactants are charged, and what reaction temperatures are chosen.

The reaction period can also vary widely depending upon the yield desired. Generally the reaction period will range from 1 hour to as much as 50 hours, or even longer. Because of the high production rates obtained with the use of the novel catalyst system, the reaction period will be shorter than that found necessary heretofore to obtain equivalent yields and conversions.

The process can be carried out in any suitable equipment. The reaction can be carried out in either a batch or a continuous fashion, with the reactants brought into contact in any order of addition. In charging the reactants and in carrying out the reaction, care should be taken to exclude air or oxygen-containing gas and moisture which tends to adversely affect the reaction. This can be accomplished by purging the reactor with dry nitrogen or other dry, inert gas prior to charging it with the reactants and catalyst and by pressuring the reactants and catalyst into the reaction vessel with such gas.

The reactants can be dried and preheated if desired and introduced separately or as a mixture into the reaction zone. After the reaction is complete the reaction mixture can be cooled, gases and vapors vented therefrom, and the reaction mixture filtered to remove catalyst and support. The liquid reaction product can be fractionally distilled or otherwise separated to obtain the desired product. Unreacted reactants can be recovered and recycled to the reaction zone if desired. The catalyst and any metalated compounds present can be inactivated or decomposed, if desired, by adding to the reaction residue a polar (active hydrogen) compound, for example, water or an alcohol such as methanol or isopropanol.

The molar ratio of alkyl aromatic reactant to monoolefin reactant can vary widely. Generally, it is preferred to employ the monoolefin in an amount greater than the stoichiometric amount. Generally, therefore, the molar ratio of alkyl aromatic reactant to monoolefin is in the range of about 0.1 to about 20, more preferably about 0.3 to about 2.

The reaction can generally be carried out with or without a diluent. Generally the diluent can be any organic compound which does not have a detrimental effect on the reaction. Examples include paraffins, cycloparaffins, and aromatics, the latter of which do not contain a hydrogen atom attached to a benzylic carbon atom. When employed the volume percent of diluent, based on the volume percent of the alkyl aromatic is in the range of about 10 to about 100. Also it is preferable if the diluent has a boiling point that is significantly different from that of the reactants and product so as to allow more easy separation of those materials, by means such as fractional distillation. Specific examples of suitable diluents include n-pentane, n-hexane, isooctane, cyclohexane, decahydronaphthalene, white oils, benzene, tertiary butylbenzene, tertiary amylbenzene, etc.

The amount of alkali metal catalyst used in the reaction will be any amount sufficient to catalyze the desired reaction. Generally the parts by weight of alkali metal employed for each 100 parts by weight of alkyl aromatic reactant will be in the range of about 0.01 to about 2, preferably about 1 to about 2.

The amount of the ingredients of the promoter composition can also vary widely. For the promoter compositions employing biphenyl and a conjugated diene there is generally employed for each 100 parts by weight of alkyl aromatic reactant about 0.1 to about 1 part by weight of conjugated diene, about 0.1 to about 2.0 parts by weight of biphenyl, and up to about 2 parts by weight of tertiary amine, preferably about 0.2 to about 0.5 part by weight of conjugated diene, about 0.2 to about 1 part by weight of biphenyl, and up to about 1 part by weight of tertiary amine. It is noted that the presence of a tertiary amine is optional in the biphenyl-conjugated diene promoter composition. For promoter compositions employing naphthalene there is generally employed for each 100 parts by weight of alkyl aromatic reactant about 0.1 to about 5 parts by weight of naphthalene and about 0.1 to about 2 parts by weight of tertiary amine, preferably about 0.2 to about 1 part by weight of naphthalene and about 0.1 to 1.0 part by weight of tertiary amine.

The instant invention and its advantages will now be further illustrated by the following examples:

EXAMPLE I

This example is a control wherein no inventive promoter is used and is typical of the procedure used in the subsequently following examples.

To a one-liter stainless steel reactor (AE Magnestir Autoclave) equipped with a stirrer, thermocouple, and inlet tubes was charged 450 milliliters (388.8 grams) of cumene (isopropylbenzene), and about 4 to 7 grams of a 22 wt.% sodium-78 wt.% potassium catalyst. The closed reactor was then stirred while heated to 190° C. Ethylene (to about 500 psig) was pressured into the reactor. The temperature was controlled by adjusting heat controls, dropping the external heater or air cooling externally. After the ethylene pressure had dropped to about 200–250 psig, more ethylene was added (again to about 500 psig). After 2–3 hours, the pressure ceased to drop. During the run, a maximum temperature of 215° C. was reached. The reactor was quenched in ice-water, the contents removed and the reactor washed with cyclohexane. The contents and washings were filtered under nitrogen and the filtrate distilled to recover the product tert-amylbenzene. A sample was obtained before filtering or washing and analyzed by GLC using a 304.8 centimeter (10 foot)×0.635 centimeter (0.25 inch) column packed with 5 wt.% SP 1200 (silicone oil) and 1.75 wt.% Bentone 34 (treated clay) on a support of Supelcoport (Supelco, Inc.) which is an acid-washed silane treated diatomite support. The chromatograph was programmed from 150°–200° C. at 10° C./min. using a 60 cubic centimeter per minute helium flow. Three such runs were made. Analysis averaged from the three runs indicated cumene was being converted at a rate of 4.6 wt.%/hr. The product selectivity was 70.6 wt.% tert-amylbenzene (TAB), 28.4 wt.% 1,1-dimethylindane (DMI), and 1.5 wt.% 1,1-dimethyl-3-ethylindane (EDMI).

EXAMPLE II

This example is another control illustrating the effects of adding a polyphenyl promoter.

The reaction described in Example I was repeated except 2 grams of biphenyl was added to the reaction mixture. The reaction initiated at 172° C., a temperature lower than the control in Example I, and cumene was consumed at a faster rate, 20.1 wt.%/hr. The selectivity was only slightly increased to 72.8 wt.% TAB with 20.0 wt.% DMI, 6.5 wt.% EDMI, and 0.7 wt.% 1,1-diethyl-3,3-dimethylindane (DEDMI).

EXAMPLE III

This example is another control and employs 1.2 grams of 1,3-butadiene instead of 2 grams of biphenyl as described in Example II. The reaction initiated at a higher temperature, than the control in Example I, 182° C., and had a significantly lower cumene rate of conversion, 14.3 wt.%, than that in Example II. The product selectivity was about the same as when no promoter was added like Example I, namely 69.6 wt.% TAB, 25.6 wt.% DMI, 4.4 wt.% EDMI.

EXAMPLE IV

This example illustrated embodiments of the present invention and shows the effect of combining 1,3-butadiene and biphenyl as a promoter composition. Also, the data listed below show the results when tertiary amines or diamines are added to the biphenyl-1,3-butadiene combination.

ture is greatly reduced while maintaining approximately the same product selectivity. One run, Example IV-C, with a ditertiary diamine present gave the lowest initiation temperature and the highest rate of cumene conversion of all the materials tested. A repeat run, Example IV-B, did not give the same cumene conversion rate. One of these latter two runs may be an anomaly, however, both clearly reflect an increase in conversion.

EXAMPLE V

This example is another control illustrating the effects of adding a polynuclear hydrocarbon initiator-promoter.

The reaction described in Example I was repeated except 1 gram of naphthalene was added to the reactor. The reaction was initiated at a much lower temperature than in Example I, 157° C., and cumene was consumed at a faster rate than in Example I, 24.2 wt.%/hr. The selectivity of tert-amylbenzene (TAB) was increased to 88.5 wt.% with only 5.5 wt.% 1,1-dimethylindane (DMI). The reaction was repeated but 4 grams of naphthalene was used. The cumene conversion was 48.2 wt.% with a selectivity of 79.1 wt.% TAB, 5.1 wt.% 1,1-dimethyl-3-ethylindane (EDMI), and 13.2 wt.% 1,1-diethyl-3,3-dimethylindane (DEDMI).

EXAMPLE VI

This example illustrates the effect of the embodiment of the invention employing naphthalene in combination with a tertiary amine.

The reaction described in Example V was repeated

Table I

Conversion of Cumene and Ethylene to Tert-Amylbenzene

| Example | Promoter[a] $\phi_2$ | Bd | TMED | TEA | Reaction Temp., °C. | Cumene Conv., %/hr. | % Selectivity by GLC[b] TAB | DMI | EDMI | DEDMI |
|---|---|---|---|---|---|---|---|---|---|---|
| I | — | — | — | — | 190–215 | 4.6[c] | 70.6[c] | 28.4[c] | 1.5[c] | — |
| II | 2.0 | — | — | — | 172–179 | 20.1 | 72.8 | 20.0 | 6.5 | 0.7 |
| III | — | 1.2 | — | — | 182–193 | 14.3 | 69.6 | 25.6 | 4.4 | — |
| Inventive Runs: | | | | | | | | | | |
| IV-A | 2.0 | 1.2 | — | — | 162–169 | 29.3 | 70.8 | 11.7 | 14.7 | 2.4 |
| -B | 2.0 | 1.5 | 1.6 | — | 169–176 | 29.1 | 74.6 | 13.4 | 9.5 | 2.5 |
| -C | 2.0 | 1.5 | 1.6 | — | 161–178 | 41.8 | 70.6 | 4.0 | 13.6 | 11.4 |
| -D | 2.0 | 1.5 | — | 1.5 | 166–178 | 27.1 | 75.1 | 15.1 | 8.0 | 1.8 |

[a]$\phi_2$=biphenyl; Bd=1,3-butadiene; TMED=N,N,N',N'-tetramethylethylenediamine; [2]TEA=triethylamine.
[b]TAB=tert-amylbenzene; DMI=1,1-dimethylindane; EDMI=1,1-dimethyl-3-ethylindane; DEDMI=1,1-diethyl-3,3-dimethylindane.
[c]Average value from three runs.

The control runs of the preceding examples are listed for comparison. The data show one of the highest rates of cumene conversion exists when biphenyl and 1,3-butadiene are used together. Also the initiation temperawith the addition of tertiary amines. The results are listed below. The results of Examples I and V are also listed for comparison:

Table II

Conversion of Cumene and Ethylene to Tert-Amylbenzene

| Example | Promoter, grams Naph[a] | TEA[B] | TMED[C] | Reaction Temp., °C. | Cumene Conv., %/hr. | % Selectivity by GLC TAB[d] | DMI[e] | EDMI[f] | DEDMI[g] |
|---|---|---|---|---|---|---|---|---|---|
| I | — | — | — | 190–215 | 4.6[h] | 70.6[h] | 28.4[h] | 1.5[h] | — |
| V-A | 1.0 | — | — | 157–163 | 24.2 | 88.5 | 5.5 | 4.9 | 1.0 |
| V-B | 4.0 | — | — | 161–178 | 48.2 | 79.1 | — | 5.1 | 13.2 |
| VI-A | 2.0 | 1.5 | — | 156–166 | 35.5 | 90.1 | — | 6.2 | 3.4 |
| VI-B | 2.0 | — | 1.5 | 155–163 | 46.7 | 84.2 | — | 4.7 | 10.5 |
| VI-C | 4.0 | — | 1.5 | 158–163 | 42.4 | 84.0 | — | 8.1 | 6.8 |

Table II-continued

| | | | Conversion of Cumene and Ethylene to Tert-Amylbenzene | | | | | | |
|---|---|---|---|---|---|---|---|---|---|
| | Promoter, grams | | | Reaction | Cumene | % Selectivity by GLC | | | |
| Example | Naph[a] | TEA[B] | TMED[C] | Temp., °C. | Conv., %/hr. | TAB[d] | DMI[e] | EDMI[f] | DEDMI[g] |
| VI-D | 2.0 | 1.5 | 1.5 | 155–164 | 39.8 | 93.1 | — | 3.4 | 3.1 |

[a]Naphthalene
[b]Triethylamine
[c]N,N,N',N'-tetramethylethylenediamine
[d]Tertiary amylbenzene
[e]1,1-Dimethylindane
[f]1,1-Dimethyl-3-ethylindane
[g]1,1-Diethyl-3,3-dimethylindane
[h]Average of 3 values.

The data in Table II indicates that raising the level of naphthalene increases the conversion rate while reducing the selectivity somewhat. The presence of the tertiary amine tends to counteract the adverse effect of the naphthalene on selectivity to give a promoter having both good conversion and selectivity.

From the foregoing description and illustrative examples, one skilled in the art can easily ascertain the essential characteristics of this invention and without departing from the spirit and scope thereof, can make various changes and modifications of the invention to adapt it to various usages and conditions. Consequently, such changes and modifications should be viewed as being within the range of equivalents of the following claims.

What is claimed is:

1. A process comprising reacting a monoolefin hydrocarbon with an alkyl aromatic compound having a hydrogen atom bonded to at least one benzylic carbon of at least one alkyl group in the presence of a catalytic amount of alkali metal and a conversion promoting amount of a promoter composition selected from the group consisting of (1) biphenyl and a conjugated diene hydrocarbon containing 4 to 12 carbon atoms per molecule, (2) biphenyl, a conjugated diene hydrocarbon containing 4 to 12 carbon atoms per molecule, and a tertiary amine and (3) naphthalene and a tertiary amine under such reaction conditions that at least one benzylic carbon of said alkyl aromatic compound is alkylated.

2. A process according to claim 1 wherein said tertiary amine is selected from those having the formula

or the formula

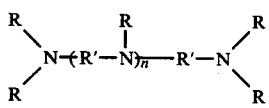

wherein R is a hydrocarbyl radical of 1 to 6 carbon atoms, R' is a divalent hydrocarbyl radical of 1 to 6 carbon atoms, n is an integer in the range of 0 to 6, and each R and R' can be the same or different.

3. A process according to claim 2 wherein said promoter composition is a biphenyl and a conjugated diene containing 4 to 12 carbon atoms per molecule.

4. A process according to claim 3 wherein said alkyl aromatic compound is an alkyl aromatic hydrocarbon having 1 to 4 alkyl substituents each having 1 to 20 carbon atoms.

5. A process according to claim 4 wherein said monoolefin hydrocarbon is selected from propylene and ethylene.

6. A process according to claim 5 wherein said conjugated diene is 1,3-butadiene.

7. A process according to claim 6 wherein for each 100 parts by weight of said alkyl aromatic hydrocarbon there is employed about 0.1 to about 1 part by weight of 1-3 butadiene, and about 0.1 to about 2 parts by weight of biphenyl, and about 1 to about 2 parts by weight of alkali metal.

8. A process according to claim 7 wherein said reaction is carried out at a temperature in the range of about 125° C. to about 225° C. and a pressure of about 50 to about 1000 psig.

9. A process according to claim 8 wherein said alkyl aromatic hydrocarbon is cumene.

10. A process according to claim 9 wherein said monoolefin is ethylene.

11. A process according to claim 10 wherein said reaction is carried out at a temperature in the range of about 140° C. to about 175° C. and a pressure of about 250 to about 600 psig.

12. A process according to claim 11 wherein for each 100 parts by weight of cumene there is employed about 0.2 to about 0.5 part by weight of 1,3-butadiene and about 0.2 to about 1 part by weight of biphenyl.

13. A process according to claim 2 wherein said promoter composition is a biphenyl, a conjugated diene containing 4 to 12 carbon atoms per molecule, and said tertiary amine.

14. A process according to claim 13 wherein said alkyl aromatic compound is an alkyl aromatic hydrocarbon having 1 to 4 alkyl substituents each having 1 to 20 carbon atoms.

15. A process according to claim 14 wherein for each 100 parts by weight of said alkyl aromatic hydrocarbon there is employed about 0.1 to about 1 part by weight of said conjugated diene, about 0.1 to about 2 parts by weight of biphenyl, about 1 to about 2 parts by weight of alkali metal and up to about 2 parts by weight of said tertiary amine.

16. A process according to claim 15 wherein said monoolefin hydrocarbon is selected from propylene and ethylene.

17. A process according to claim 16 wherein said conjugated diene is 1,3-butadiene.

18. A process according to claim 17 wherein said reaction is carried out at a temperature in the range of about 125° C. to about 225° C. and a pressure of about 50 to about 1000 psig.

19. A process according to claim 18 wherein said tertiary amine is triethylamine or N,N,N',N'-tetramethylethylenediamine.

20. A process according to claim 19 wherein said alkyl aromatic hydrocarbon is cumene.

21. A process according to claim 20 wherein said monoolefin is ethylene.

22. A process according to claim 21 wherein said reaction is carried out at a temperature in the range of about 140° C. to about 175° C. and a pressure of about 250 to about 600 psig.

23. A process according to claim 22 wherein for each 100 parts by weight of cumene there is employed about 0.2 to about 0.5 part by weight of 1,3-butadiene, and about 0.2 to about 1 part by weight of biphenyl, and up to about 1 part by weight of tertiary amine.

24. A process according to claim 23 wherein said tertiary amine is N,N,N',N'-tetramethylethylene diamine.

25. A process according to claim 2 wherein said promoter composition is a naphthalene and said tertiary amine.

26. A process according to claim 25 wherein said alkyl aromatic compound is an alkyl aromatic hydrocarbon having 1 to 4 alkyl substituents each having 1 to 20 carbon atoms.

27. A process according to claim 26 wherein for each 100 parts by weight of said alkyl aromatic hydrocarbon there is employed about 0.1 to about 5 parts by weight of naphthalene, and about 0.1 to about 2 parts by weight of said tertiary amine, and about 1 to about 2 parts by weight of alkali metal.

28. A process according to claim 27 wherein said monoolefin hydrocarbon is selected from propylene and ethylene.

29. A process according to claim 28 wherein said conjugated diene is 1,3-butadiene.

30. A process according to claim 29 wherein said reaction is carried out at a temperature in the range of about 125° C. to about 225° C. and a pressure of about 50 to about 1000 psig.

31. A process according to claim 30 wherein said alkyl aromatic hydrocarbon is cumene.

32. A process according to claim 31 wherein said monoolefin is ethylene.

33. A process according to claim 32 wherein said reaction is carried out at a temperature in the range of about 140° C. to about 175° C. and a pressure of about 250 to about 600 psig.

34. A process according to claim 33 wherein for each 100 parts by weight of cumene there is employed about 0.2 to about 1 part by weight of naphthalene and about 0.1 to about 1 part by weight of tertiary amine.

35. A process according to claim 33 wherein said tertiary amine is N,N,N',N'-tetramethylethylenediamine.

36. A process according to claim 30 wherein said tertiary amine is N,N,N',N'-tetramethylethylenediamine.

37. A process according to claim 30 wherein said tertiary amine is triethylamine.

38. A process according to claim 30 wherein said alkali metal is a sodium-potassium alloy.

* * * * *